United States Patent
Tomita et al.

(10) Patent No.: US 9,481,298 B2
(45) Date of Patent: Nov. 1, 2016

(54) REPORTING SYSTEM, REPORTING CONTROL METHOD, AND HANDHELD DEVICE

(71) Applicants: Yosuke Tomita, Aichi (JP); Manabu Sakai, Aichi (JP); Takahiro Inaguma, Aichi (JP); Koji Takizawa, Aichi (JP)

(72) Inventors: Yosuke Tomita, Aichi (JP); Manabu Sakai, Aichi (JP); Takahiro Inaguma, Aichi (JP); Koji Takizawa, Aichi (JP)

(73) Assignee: OMRON AUTOMOTIVE ELECTRONICS CO., LTD., Aichi (JP)

( * ) Notice: Subject to any disclaimer, the term of this patent is extended or adjusted under 35 U.S.C. 154(b) by 57 days.

(21) Appl. No.: 14/327,308

(22) Filed: Jul. 9, 2014

(65) Prior Publication Data
US 2015/0015385 A1 Jan. 15, 2015

(30) Foreign Application Priority Data
Jul. 9, 2013 (JP) .................................. 2013-143178

(51) Int. Cl.
| | | |
|---|---|---|
| B60Q 1/00 | (2006.01) | |
| B60Q 9/00 | (2006.01) | |
| G08G 1/00 | (2006.01) | |
| H04M 1/66 | (2006.01) | |
| G06Q 50/10 | (2012.01) | |

(Continued)

(52) U.S. Cl.
CPC ................ *B60Q 9/00* (2013.01); *G08G 1/205* (2013.01); *G06Q 50/10* (2013.01); *G06Q 50/22* (2013.01); *G08B 25/001* (2013.01); *G08B 25/006* (2013.01); *H04M 1/66* (2013.01)

(58) Field of Classification Search
CPC ...... G08G 1/205; G06Q 50/10; G06Q 50/22; H04M 1/66; H04M 1/6091; H04M 1/72569; H04M 1/72577
USPC ............................................ 340/436, 539.18
See application file for complete search history.

(56) References Cited

U.S. PATENT DOCUMENTS

| | | | | |
|---|---|---|---|---|
| 5,311,197 A | * | 5/1994 | Sorden ................. | B60R 25/102 342/357.31 |
| 5,334,974 A | * | 8/1994 | Simms .................. | B60R 25/102 340/426.18 |
| 5,629,693 A | * | 5/1997 | Janky .................... | B60R 25/102 180/287 |

(Continued)

FOREIGN PATENT DOCUMENTS

| | | |
|---|---|---|
| DE | 10 2009 037 086 A1 | 2/2011 |
| JP | 2001-250183 A | 9/2001 |

(Continued)

OTHER PUBLICATIONS

Office Action in counterpart German Patent Application No. 10 2014 213 254.1 issued Jun. 30, 2015 (12 pages)

*Primary Examiner* — Firmin Backer
*Assistant Examiner* — Adnan Aziz
(74) *Attorney, Agent, or Firm* — Osha Liang LLP

(57) ABSTRACT

A reporting system has a first handheld device that locks and unlocks a door of a vehicle, and a second handheld device that communicates with the first handheld device. The first handheld device has an inside/outside determination unit that carries out wireless communication with the vehicle and acquires, with the vehicle, information of inside/outside determination on whether the first handheld device is inside the vehicle or outside the vehicle, and a transmitting unit that transmits the result of the inside/outside determination. The second handheld device has a receiving unit that receives the result of the determination from the first handheld device.

17 Claims, 7 Drawing Sheets

(51) Int. Cl.
*G06Q 50/22* (2012.01)
*G08B 25/00* (2006.01)

(56) References Cited

U.S. PATENT DOCUMENTS

| | | | | |
|---|---|---|---|---|
| 5,914,675 | A * | 6/1999 | Tognazzini | G01S 5/0027 340/426.19 |
| 7,308,272 | B1 * | 12/2007 | Wortham | G01S 19/17 342/357.55 |
| 7,895,063 | B2 * | 2/2011 | Wahlbin | G06Q 40/02 705/2 |
| 8,421,589 | B2 * | 4/2013 | Sultan | B60R 25/1003 340/426.13 |
| 8,754,766 | B2 * | 6/2014 | Oesterling | H04W 4/22 340/436 |
| 8,878,661 | B2 * | 11/2014 | Inaguma | H04B 5/0031 340/438 |
| 9,043,049 | B2 * | 5/2015 | Reich | B60R 16/037 701/2 |
| 9,102,220 | B2 * | 8/2015 | Breed | B60R 21/0132 |
| 2005/0037730 | A1 * | 2/2005 | Montague | B60R 25/1004 455/404.2 |
| 2005/0107673 | A1 * | 5/2005 | Ball | A61B 5/411 600/301 |
| 2007/0279200 | A1 * | 12/2007 | Morimoto | G06Q 50/10 340/436 |
| 2008/0176537 | A1 * | 7/2008 | Smoyer | G08G 1/205 455/414.1 |
| 2008/0242261 | A1 * | 10/2008 | Shimanuki | G08B 17/00 455/404.2 |
| 2011/0117877 | A1 * | 5/2011 | Ghazarian | H04M 1/72538 455/404.2 |
| 2011/0275321 | A1 * | 11/2011 | Zhou | H04M 1/6091 455/41.2 |
| 2013/0109342 | A1 * | 5/2013 | Welch | B60N 2/002 455/404.2 |
| 2013/0194087 | A1 * | 8/2013 | Tomer | G08G 1/205 340/436 |
| 2013/0211623 | A1 * | 8/2013 | Thompson | G07C 5/008 701/2 |
| 2014/0099899 | A1 * | 4/2014 | Jamal-Syed | H04L 63/0492 455/41.2 |
| 2014/0132404 | A1 * | 5/2014 | Katoh | B60R 21/013 340/436 |
| 2014/0253288 | A1 * | 9/2014 | O'Brien | G07C 9/00309 340/5.61 |
| 2014/0302810 | A1 * | 10/2014 | Inha | H04W 4/005 455/404.1 |

FOREIGN PATENT DOCUMENTS

| | | |
|---|---|---|
| JP | 2011-144624 A | 7/2011 |
| WO | 2006085380 A1 | 8/2006 |
| WO | 2010/051455 A2 | 5/2010 |

* cited by examiner

REPORTING SYSTEM, REPORTING CONTROL METHOD, AND HANDHELD DEVICE

BACKGROUND OF THE INVENTION

1. Field of the Invention

The present invention relates to a reporting system, a reporting control method and a handheld device, and particularly to a reporting system, a reporting control method and a handheld device for automatic reporting at the occurrence of a vehicle accident.

2. Description of Related Art

According to the related art, a system is proposed in which if a vehicle receives an impact of an accident with an onboard device detecting the occurrence thereof, the onboard device causes a mobile phone to dial a specific reporting number, thus enabling automatic reporting at the occurrence of an accident (see, for example, JP-A-2001-250183). Specifically, as a user carrying a mobile phone gets into the vehicle, the mobile phone and the onboard device carry out linking processing based on Bluetooth (trademark registered), hold a linked state and stand by. Then, if the onboard device detects the occurrence of an accident, the onboard device transmits information about the accident to the mobile phone. The mobile phone dials a specific reporting number and reports the occurrence of the accident to an accident information center.

Also, a technique is proposed in which a mobile phone with having a shock sensor automatically reports positional information or the like to an emergency contact number upon detecting an impact of a vehicle accident or the like in a predetermined level or higher (see, for example, WO2006/085380).

Moreover, according to the related art, a technique is proposed in which a vehicle key FOB calculates the strength of magnetic fields generated by radio waves from antennas on the side of the driver's seat as well as the side of the front passenger seat in the vehicle so that the vehicle is notified of the result of the calculation to determine the position of the key FOB based on the difference in the strength of the magnetic fields (see, for example, JP-A-2011-144624).

However, in the case where the mobile phone detects an impact as in the technique disclosed in WO2006/085380, it may be difficult to discriminate whether the impact is due to a vehicle accident or due to other causes than an accident, such as falling of the mobile phone itself. Therefore, there is a risk such that automatic reporting is carries out mistakenly despite the absence of an accident.

SUMMARY OF THE INVENTION

Thus, one or more embodiments of the present invention improves accuracy of automatic reporting by a handheld device such as a mobile phone at the occurrence of a vehicle accident.

According to one or more embodiments of the invention, a reporting system includes: a first handheld device used to lock and unlock a door of a vehicle; and a second handheld device configured to communicate with the first handheld device. The first handheld device includes: an inside/outside determination unit which carries out wireless communication with the vehicle to acquire information of inside/outside determination on whether the first handheld device is inside the vehicle or outside the vehicle; and a transmitting unit which transmits the result of the inside/outside determination. The second handheld device includes: a receiving unit which receives the result of the determination from the first handheld device; a mode setting unit which sets a first mode in which automatic reporting about a vehicle accident is carried out, if the result of the determination indicates being inside the vehicle, and which sets a second mode in which the automatic reporting is not carried out, if the result of the determination indicates being outside the vehicle; an impact detecting unit which carries out detection of an impact on the second handheld device; and a reporting unit which carries out the automatic reporting when an impact of a predetermined strength or greater on the second handheld device is detected in the case where the first mode is set.

In the reporting system according to one or more embodiments of the invention, by the first handheld device, wireless communication with the vehicle is carried, information about inside/outside determination on whether the first handheld device is inside the vehicle or outside the vehicle is acquired with the vehicle, and the result of the inside/outside determination is transmitted. By the second handheld device, the result of the determination is received from the first handheld device, and if the result of the determination indicates being inside the vehicle, the first mode is set in which automatic reporting about a vehicle accident is carried out, whereas if the result of the determination indicates being outside the vehicle, the second mode is set in which the automatic reporting is not carried out. Detection of an impact on the second handheld device is carried out, and when an impact of a predetermined strength or greater on the second handheld device is detected in the case where the first mode is set, the automatic reporting is carried out.

Therefore, accuracy of the automatic reporting by the second handheld device at the occurrence of a vehicle accident can be improved.

The first handheld device may include, for example, a vehicle key FOB. The second handheld device may include, for example, a high-function mobile phone such as smartphone, or a tablet computer or the like. The inside/outside determination unit may include, for example, an arithmetic unit such as CPU. The transmitting unit may include, for example, a communication device that carries out wireless communication. The receiving unit may include, for example, a communication device that carries out wireless communication. The mode setting unit may include, for example, an arithmetic unit such as CPU. The impact detecting unit may include, for example, an impact sensor, vibration sensor, acceleration sensor or the like. The reporting unit may include, for example, an arithmetic unit such as CPU and a communication device that carries out mobile communication.

The first handheld device can be a key FOB used for remote controls to lock and unlock a door of the vehicle, and the second handheld device can be a mobile phone.

The first mode can be a state where an application program to carry out the automatic reporting is started up, and the second mode can be a state where the application program is not started up.

Thus, highly accurate automatic reporting is possible simply by installing the application program in the second handheld device.

The communication between the first handheld device and the second handheld device can be short-range wireless communication, and the second handheld device can carry out the automatic reporting to a predetermined center via a mobile communication network.

Thus, there is an increased possibility that the second handheld device is inside the vehicle or outside the vehicle together with the first handheld device. This improves accuracy of the automatic reporting. Also, the automatic reporting can be carried out securely via the mobile communication network.

The inside/outside determination unit can receive the result of the determination from the vehicle.

Thus, the first handheld device does not need to carry out the inside/outside determination. This can reduce the processing load on the first handheld device.

The inside/outside determination unit can carry out the inside/outside determination based on the result of wireless communication with the vehicle.

Thus, since the first handheld device carries out the inside/outside determination, the first handheld device and the second handheld device can acquire the result of the inside/outside determination more securely.

According to one or more embodiments of the invention, a reporting control method includes: an inside/outside determination step and a transmission step executed by a key FOB used to lock and unlock a door of a vehicle; the inside/outside determination step including carrying out wireless communication with a vehicle and acquiring, with the vehicle, information about inside/outside determination on whether the key FOB is inside the vehicle or outside the vehicle; the transmission step including transmitting the result of the inside/outside determination; and a receiving step, a mode setting step, an impact detection step, and reporting step executed by a handheld device configured to communicate with the key FOB; the receiving step including receiving the result of the determination from the key FOB; the mode setting step including setting a first mode in which automatic reporting about a vehicle accident is carried out, if the result of the determination indicates being inside the vehicle, and setting a second mode in which the automatic reporting is not carried out, if the result of the determination indicates being outside the vehicle; the impact detection step including detecting an impact on the handheld device; and the reporting step including carrying out the automatic reporting when an impact of a predetermined strength or greater on the handheld device is detected in the case where the first mode is set.

In the reporting control method according to one or more embodiments of the invention, by the key FOB, wireless communication with the vehicle is carried out, information about inside/outside determination on whether the key FOB is inside the vehicle or outside the vehicle is acquired with the vehicle, and the result of the inside/outside determination is transmitted. By the handheld device, the result of the determination is received from the key FOB, and if the result of the determination indicates being inside the vehicle, the first mode is set in which an automatic reporting about a vehicle accident is carried out, whereas if the result of the determination indicates being outside the vehicle, the second mode is set in which the automatic reporting is not carried out. Detection of an impact on the handheld device is carried out, and when an impact of a predetermined strength or greater on the handheld device is detected in the case where the first mode is set, the automatic reporting is carried out.

Therefore, accuracy of the automatic reporting by the handheld device at the occurrence of a vehicle accident can be improved.

The handheld device may include, for example, a high-function mobile phone such as smartphone or a tablet computer or the like.

According to one or more embodiments of the invention, a handheld device includes: an inside/outside determination result storage unit which stores, based on the result of communication with a vehicle, the result of inside/outside determination on whether the handheld device is inside the vehicle or outside the vehicle; an impact detecting unit which carries out detection of an impact; and a reporting unit which carries out reporting if the impact detecting unit detects an impact and the inside/outside determination storage unit stores that the handheld device is inside the vehicle.

In the handheld device according to one or more embodiments of the invention, the result of inside/outside determination on whether the handheld device is inside the vehicle or outside the vehicle is stored, based on the result of communication with the vehicle, and detection of an impact is carried out. If an impact is detected and information that the handheld device is inside the vehicle is stored, reporting is carried out.

Therefore, accuracy of the automatic reporting by the handheld device at the occurrence of a vehicle accident can be improved.

The handheld device may include, for example, a high-function mobile phone such as smartphone, a tablet computer, a vehicle key FOB or the like. The inside/outside determination result storage unit may include, for example, an arithmetic unit such as CPU, or a storage device or the like. The impact detecting unit may include, for example, an impact sensor, vibration sensor, acceleration sensor or the like. The reporting unit may include, for example, an arithmetic unit such as CPU and a communication device that carries out mobile communication.

According to one or more embodiments of the invention, a handheld device includes: a receiving unit which receives information about inside/outside determination on whether a key FOB used to lock and unlock a door of a vehicle is inside the vehicle or outside the vehicle, from the key FOB; a mode setting unit which sets a first mode in which automatic reporting about a vehicle accident is carried out, if the key FOB is inside the vehicle, and which sets a second mode in which the automatic reporting is not carried out, if the key FOB is outside the vehicle; an impact detecting unit which carries out detection of an impact; and a reporting unit which carries out the automatic reporting when an impact of a predetermined strength or greater on the impact detecting unit is detected in the case where the first mode is set.

In the handheld device according to one or more embodiments of the invention, the result of inside/outside determination on whether a key FOB used to lock and unlock a door of a vehicle is inside the vehicle or outside the vehicle is received from the key FOB. If the key FOB is inside the vehicle, a first mode is set in which automatic reporting about a vehicle accident is carried out. If the key FOB is outside the vehicle, a second mode is set in which the automatic reporting is not carried out. Detection of an impact is carried out, and when an impact of a predetermined strength or greater is detected in the case where the first mode is set, the automatic reporting is carried out.

Therefore, accuracy of the automatic reporting by the handheld device at the occurrence of a vehicle accident can be improved.

The handheld device may include, for example, a high-function mobile phone such as smartphone, or a tablet computer or the like. The receiving unit may include, for example, a communication device that carries out wireless communication. The mode setting unit may include, for example, an arithmetic unit such as CPU. The impact detecting unit may include, for example, an impact sensor, vibration sensor, acceleration sensor or the like. The reporting unit may include, for example, an arithmetic unit such as CPU and a communication device that carries out mobile communication.

The first mode can be a state where an application program to carry out the automatic reporting is started up, and the second mode can be a state where the application program is not started up.

Thus, highly accurate automatic reporting is possible simply by installing the application program in the handheld device.

According to one or more embodiments of the invention, automatic reporting about a vehicle accident can be carried out. Particularly, according to one or more embodiments of the invention, accuracy of the automatic reporting by a handheld device at the occurrence of a vehicle accident can be improved.

DETAILED DESCRIPTION

Hereinafter, embodiments of the invention will be described. The embodiments will be described in the following order. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention.
1. Embodiments
2. Modifications
1. Embodiments
Example of Configuration of Reporting System 1

Figure 1:
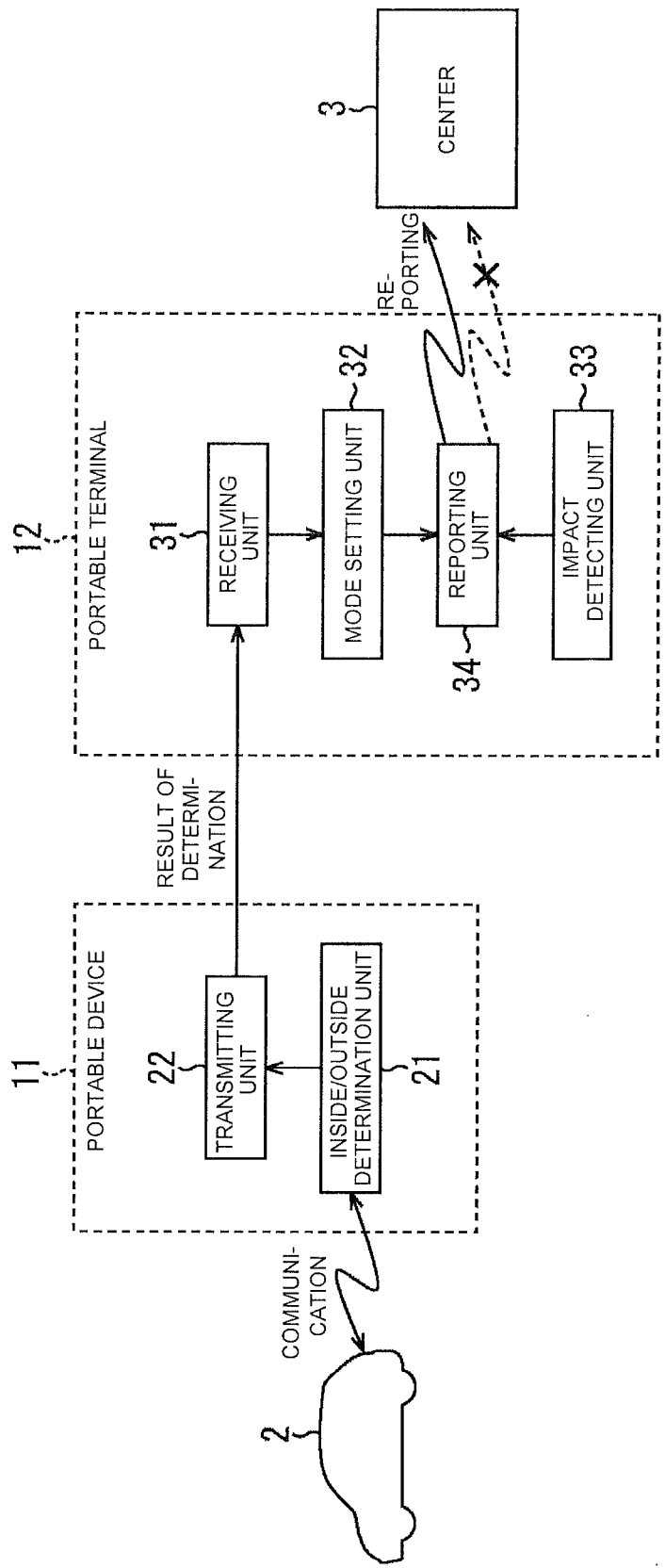
FIG. 1 is a block diagram showing a reporting system to which one or more embodiments of the invention is applied.

FIG. 1 is a block diagram showing a reporting system 1 according to one or more embodiments of the present invention.

The reporting system 1 is a system applied to a vehicle 2 and is configured to include a handheld device 11 (first handheld device) and a handheld device 12 (second handheld device). The reporting system 1 can be applied to the vehicle 2 of any type.

The handheld device 11 may include, for example, a key FOB used to operate a device installed in the vehicle 2. For example, the handheld device 11 carries out wireless communication with the vehicle 2 and thereby causes the vehicle 2 to execute a predetermined function such as keyless entry, passive entry or push start.

Here, keyless entry is a function in which the handheld device 11 is operated to carry out a remote control to lock or unlock a door of the vehicle 2 without using any physical key. Also, passive entry is a function to lock or unlock a door when the handheld device 11 is detected near the door in the case where a door handle of the vehicle 2 or a button near the door or the like is operated. Moreover, push start is a function to cancel start restraint of the vehicle 2 by an immobilizer and enable the vehicle 2 to start, when the handheld device 11 is detected inside the vehicle in the case where a start switch or the like inside the vehicle is pressed.

The handheld device 11 is configured to include an inside/outside determination unit 21 and a transmitting unit 22.

The inside/outside determination unit 21 carries out wireless communication with the vehicle 2 and acquires, with the vehicle 2, information about inside/outside determination on whether the handheld device 11 is in the vehicle 2 (inside the vehicle) or out of the vehicle 2 (outside the vehicle). Then, the inside/outside determination unit 21 notifies the transmitting unit 22 of the result of the inside/outside determination.

Any technique can be employed for the inside/outside determination. For example, the vehicle 2 and the inside/outside determination unit 21 carry out wireless communication in LF range or UHF range via one or more antennas provided on the vehicle 2. Then, based on information such as whether communication between the two is possible or not, the receiving intensity on the side of the vehicle 2, the receiving intensity on the side of the handheld device 11, and the position(s) of the antenna(s) on the vehicle 2 with which the handheld device 11 communicates, the inside/outside determination is carried out, for example, using a known technique.

Also, the inside/outside determination may be carried out by the vehicle 2 or by the handheld device 11. If the inside/outside determination is carried out by the vehicle 2, information of the inside/outside determination carried out by the vehicle 2 is transmitted from the vehicle 2 to the handheld device 11. Then, the inside/outside determination unit 21 of the handheld device 11 stores the acquired information as information of its own inside/outside determination. In this case, the inside/outside determination unit 21 operates as an inside/outside determination result storage unit which stores the acquired information of the inside/outside determination (the result of the inside/outside determination).

Meanwhile, if the inside/outside determination is carried out by the handheld device 11, for example, the inside/outside determination unit 21 carries out inside/outside determination processing by detecting which transmission antenna on the side of the vehicle 2 the received signal is transmitted from, or the like, and thus acquires the information of the inside/outside determination.

The transmitting unit 22 carries out wireless communication of a predetermined system with the handheld device 12 and transmits the result of the inside/outside determination to the handheld device 12.

For the wireless communication between the handheld device 11 and the handheld device 12, short-range wireless communication in which the communication range is limited to a short range, for example, Bluetooth (trademark registered), Bluetooth low energy, infrared communication, NFC (near field communication) or the like, is employed.

The handheld device 12 may include, for example, a portable communication terminal configured to carry out mobile communication via a mobile communication network (for example, a mobile phone network or the like), such as a mobile phone, satellite phone, PHS or the like. More specifically, the handheld device 12 may include, for example, a mobile phone (including smartphone, PHS or the like), or a tablet computer or the like. Also, the mobile communication carried out by the handheld device 12 includes audio communication and data communication. When the user drives the vehicle 2, the user is likely to get into the vehicle 2, carrying both the handheld device that is the key to the vehicle 2 and the handheld device 12 including a mobile phone or the like, at the same time.

The handheld device 12 is configured to include a receiving unit 31, a mode setting unit 32, an impact detecting unit 33, and a reporting unit 34.

The receiving unit 31 receives the result of the inside/outside determination from the handheld device 11 and supplies the result of the inside/outside determination to the mode setting unit 32.

The mode setting unit 32 carries out setting of a reporting mode indicating whether the reporting unit 34 carries out automatic reporting about an accident of the vehicle 2 or not, based on the result of the inside/outside determination. Specifically, the mode setting unit 32 sets an automatic reporting mode in which automatic reporting is carried out, or a normal mode in which automatic reporting is not carried out.

The automatic reporting mode is, for example, a state where a dedicated application to carry out automatic reporting (hereinafter referred to as an automatic reporting program) is started up. Meanwhile, the normal mode is a state where the automatic reporting program is not started up and is the normal state of use of the handheld device 12. For example, the mode setting unit 32 starts up the automatic reporting program and thereby sets the automatic reporting mode. The mode setting unit 32 stops the automatic reporting program and thereby sets the normal mode. Therefore, the handheld device 12 carries out automatic reporting only in the state where the automatic reporting program is started up.

The impact detecting unit 33 may include a sensor configured to detect an impact, for example, an impact sensor, vibration sensor, acceleration sensor or the like, and detects an impact on the handheld device 12. The impact detecting unit 33 supplies sensor data indicating the strength of the detected impact to the reporting unit 34.

The reporting unit 34 carries out reporting about an accident of the vehicle 2 to a center 3 which accepts reporting about a vehicle accident, via a mobile communication network. Specifically, the reporting unit 34 determines whether there is a possibility that an accident of the vehicle 2 has occurred or not, based on the sensor data from the impact detecting unit 33. Then, if the reporting unit 34 determines that there is a possibility that an accident has occurred, the reporting unit 34 automatically reports to the center 3 when the automatic reporting mode is set, and the reporting unit 34 does not automatically report to the center 3 when the normal mode is set.

For the reporting by the handheld device 12 to the center 3, for example, an emergency reporting system via a mobile communication network such as e-Call is used.

Processing in Reporting System 1

Figure 2:
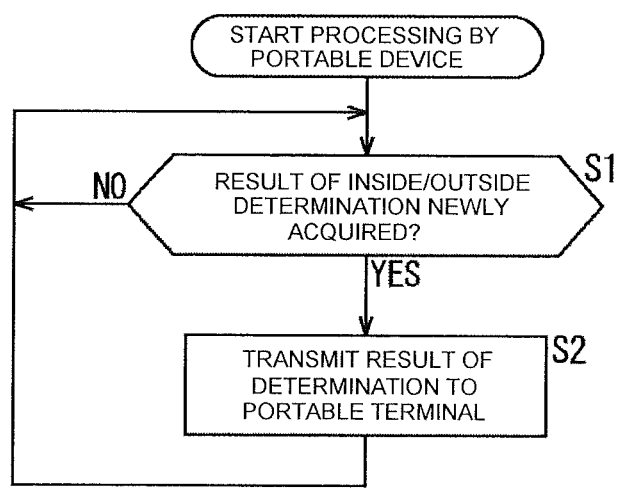
FIG. 2 is a flowchart for explaining a first embodiment of processing by a handheld device.
Figure 3:
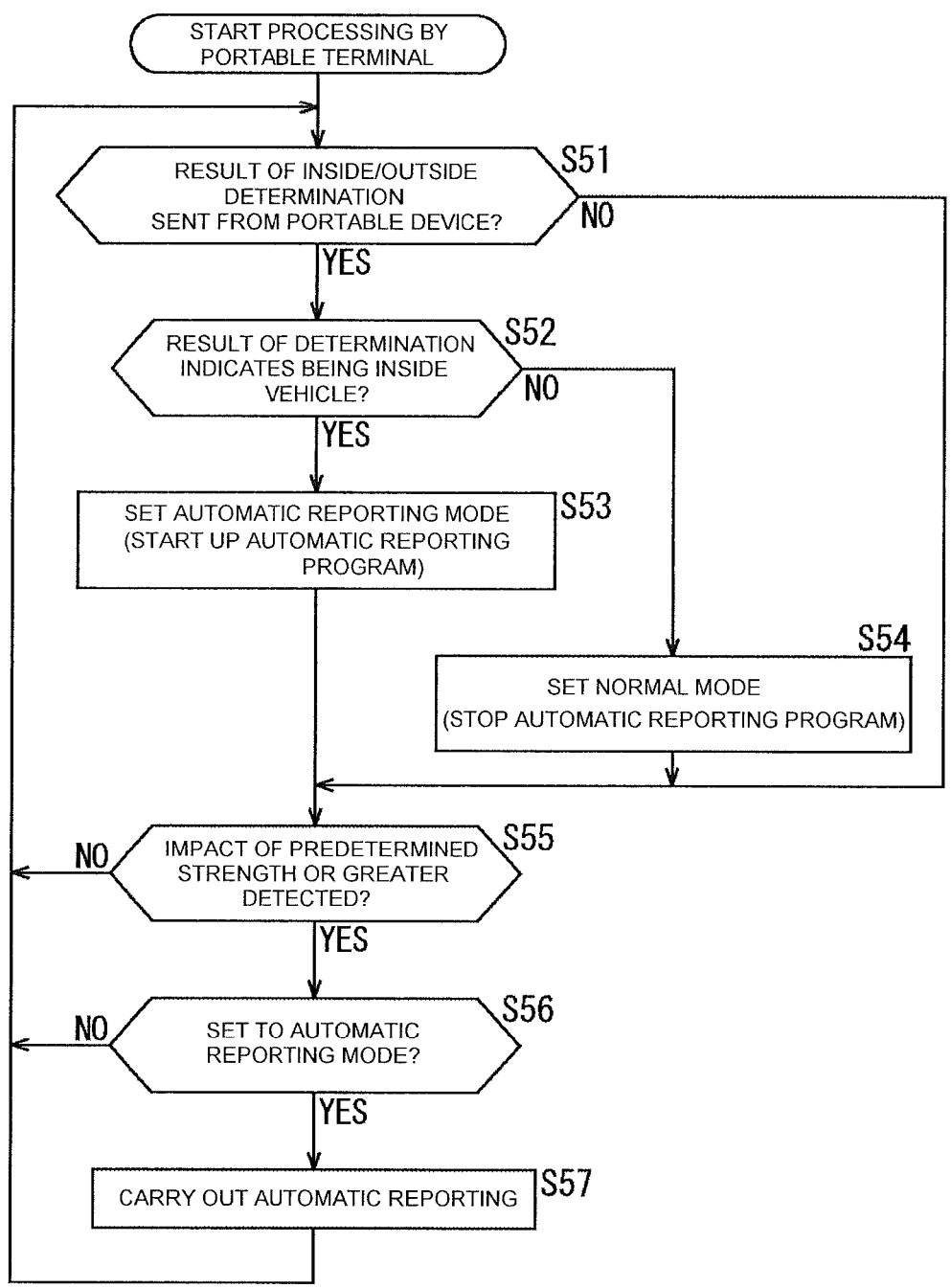
FIG. 3 is a flowchart for explaining processing by a handheld device.
Figure 4:
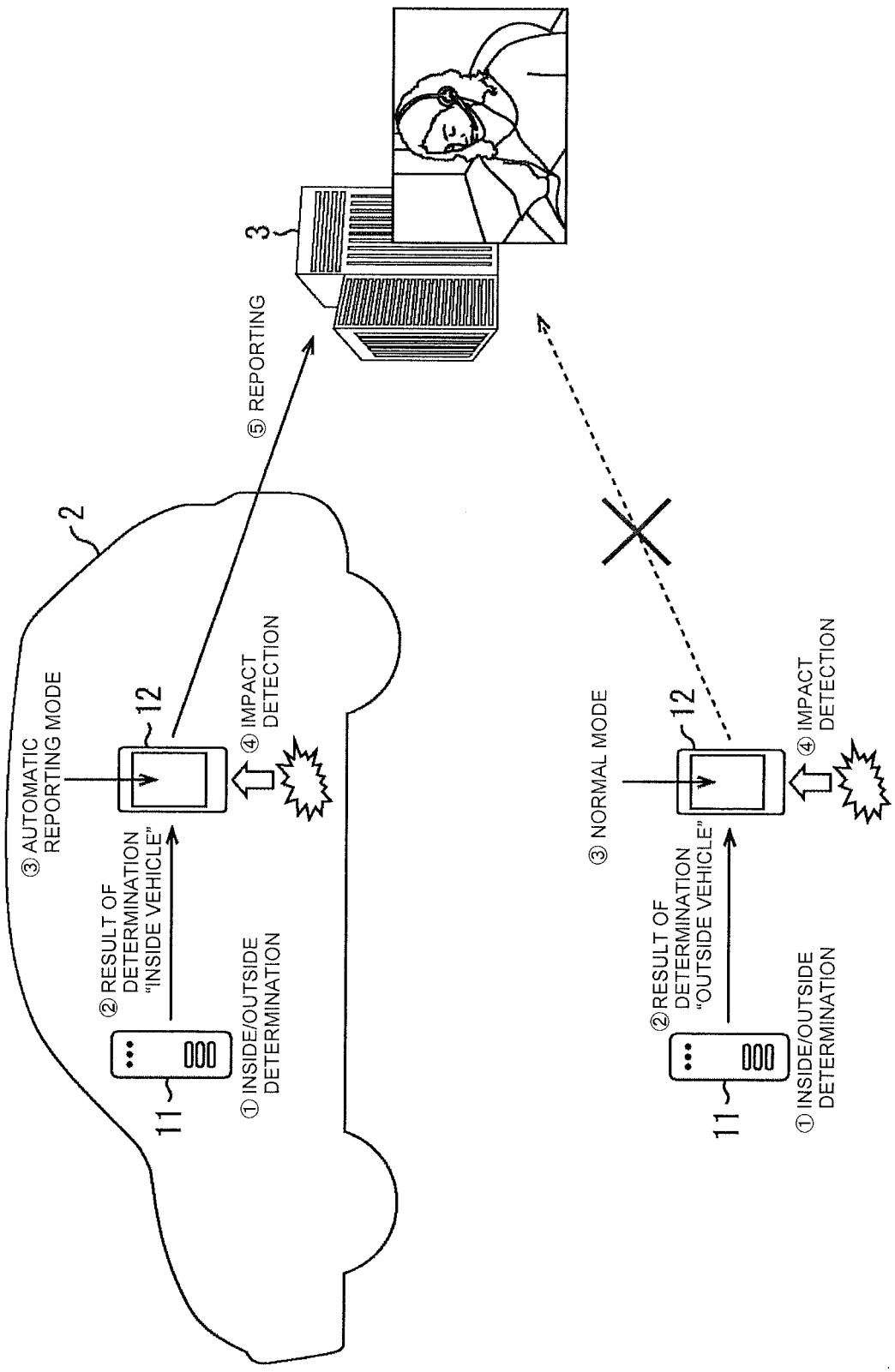
FIG. 4 illustrates a flow of processing in a reporting system.

Next, processing in the reporting system 1 will be described with reference to FIGS. 2 to 4. FIG. 2 is a flowchart for explaining processing by the handheld device 11. FIG. 3 is a flowchart for explaining processing by the handheld device 12. FIG. 4 illustrates a flow of processing.

First, the processing by the handheld device 11 will be described with reference to FIGS. 2 and 4.

In step S1, the inside/outside determination unit 21 determines whether the result of inside/outside determination is newly acquired or not. This determination processing is executed periodically, for example, until it is determined that the result of inside/outside determination is newly acquired.

Then, for example, if the inside/outside determination unit 21 receives a polling signal transmitted periodically from one or more antennas provided on the vehicle 2, the inside/outside determination unit 21 transmits a response signal to the vehicle 2. At this point, the response signal may include the receiving intensity of the polling signal.

The vehicle 2 carries out inside/outside determination about the handheld device 11, for example, based on information such as the receiving intensity of the response signal from the handheld device 11, the receiving intensity of the polling signal at the handheld device 11, or the position of the antenna of the transmission source of the polling signal received by the handheld device 11. Then, if the inside/outside determination is successful, the vehicle 2 transmits the result of the determination to the handheld device 11. If the inside/outside determination unit 21 receives the result of the determination, the inside/outside determination unit 21 determines that the result of inside/outside determination is newly acquired, and the processing goes to step S2.

Alternatively, for example, if the inside/outside determination unit 21 receives a polling signal transmitted periodically from one or more antennas provided on the vehicle 2, the inside/outside determination unit 21 carries out inside/outside determination about the handheld device 11 on its own, based on information such as the receiving intensity of the polling signal or the position of the antenna of the transmission source of the received polling signal. Then, if the inside/outside determination is successful, the inside/outside determination unit 21 determines that the result of inside/outside determination is newly acquired, and the processing goes to step S2.

In step S2, the handheld device 11 transmits the result of the determination to the handheld device 12. Specifically, the inside/outside determination unit 21 notifies the transmitting unit 22 of the result of the determination. The transmitting unit 22 establishes communication with the handheld device and then transmits the result of the determination to the handheld device 12. The communication with the handheld device 12 may be established in advance.

Thus, if the handheld device 11 is in the vehicle 2, the result of the inside/outside determination indicating "inside vehicle" is sent from the handheld device 11 to the handheld device 12, as shown on the top left-hand side of FIG. 4. Meanwhile, if the handheld device 11 is out of the vehicle 2, the result of the inside/outside determination indicating "outside vehicle" is sent from the handheld device 11 to the handheld device 12, as shown on the bottom left-hand side of FIG. 4.

After that, the processing returns to step S1 and the processing of step S1 and onward is executed.

In this way, if wireless communication between the vehicle and the handheld device 11 is possible, inside/outside determination is carried out periodically. If the inside/outside determination is successful, the result of the determination is sent from the handheld device 11 to the handheld device 12.

Next, the processing executed by the handheld device 12, corresponding to the processing by the handheld device 11 shown in FIG. 2, will be described with reference to FIGS. 3 and 4.

In step S51, the receiving unit 31 determines whether the result of the inside/outside determination is sent from the handheld device 11 or not. If the receiving unit 31 receives the result of the determination sent from the handheld device 11 in step S2 of FIG. 2, the receiving unit 31 determines that the result of the inside/outside determination is sent from the handheld device 11, and the processing goes to step S52.

In step S52, the mode setting unit 32 determines whether the result of the determination indicates being inside the vehicle or not. Specifically, the receiving unit 31 supplies the result of the determination received from the handheld device 11, to the mode setting unit 32. Then, if the mode setting unit 32 determines that the result of the determination indicates being inside the vehicle, the processing goes to step S53.

In step S53, the mode setting unit 32 sets the automatic reporting mode. That is, if the handheld device 11 is inside the vehicle, the handheld device 12 is set to the automatic reporting mode, as shown on the top left-hand side of FIG. 4. At this point, since the communication range between the handheld device 11 and the handheld device 12 is limited to a short range, the handheld device 12, too, is likely to be inside the vehicle.

After that, the processing goes to step S55.

Meanwhile, if it is determined in step S52 that the result of the determination indicates being outside the vehicle, the processing goes to step S54.

In step S54, the mode setting unit 32 sets the normal mode. That is, if the handheld device 11 is outside the vehicle, the handheld device 12 is set to the normal mode, as shown on the bottom left-hand side of FIG. 4. At this point, since the communication range between the handheld device 11 and the handheld device 12 is limited to a short range, the handheld device 12, too, is likely to be outside the vehicle.

After that, the processing goes to step S55.

Meanwhile, if it is determined in step S51 that the result of the inside/outside determination is not sent from the handheld device 11, the processing of steps S52 to S54 is skipped and the processing goes to step S55.

In step S55, the reporting unit 34 determines whether an impact of a predetermined strength or greater is detected or not. Specifically, if the strength indicated by the sensor data supplied from the impact detecting unit 33 is a predetermined threshold or above, the reporting unit 34 determines that an impact of a predetermined strength or greater is detected, and the processing goes to step S56.

This threshold is set at a value suitable for detecting the occurrence of an accident of the vehicle 2. For example, this threshold is set, for example, at a value that is greater than the strength of an impact expected to be applied on the handheld device 12 when the handheld device 12 falls in the vehicle 2 and smaller than the strength of an impact expected to be applied on the handheld device 12 when an accident of the vehicle 2 has occurred. Also, this threshold may be a fixed value or may be changed by the user.

In step S56, the reporting unit 34 determines whether the automatic reporting mode is set or not. Specifically, the impact detecting unit 33 notifies the reporting unit 34 that an impact of a predetermined strength or greater is detected. Then, if the reporting unit 34 determines that the automatic reporting mode is set, the processing goes to step S57.

In step S57, the reporting unit 34 carries out automatic reporting. Specifically, the reporting unit 34 automatically reports to the center 3 that there is a possibility that an accident of the vehicle 2 has occurred, via a mobile communication network. That is, if the handheld device 11 is inside the vehicle and the handheld device 12 is set to the automatic reporting mode, as shown on the top left-hand side of FIG. 4, reporting from the handheld device 12 to the center 3 is automatically carried out when an impact of a predetermined strength or greater on the handheld device 12 is detected.

At this point, along with the reporting, the positional information of the vehicle 2 acquired or held by the handheld device 12, image data showing the status of the vehicle 2 and the like may also be transmitted to the center 3.

After that, the processing returns to step S51 and the processing of step S51 and onward is executed.

Meanwhile, if it is determined in step S56 that the normal mode is set, automatic reporting is not carried out and the processing returns to step S51. That is, if the handheld device 11 is outside the vehicle and the handheld device 12 is set to the normal mode, as shown on the bottom left-hand side of FIG. 4, reporting from the handheld device 12 to the center 3 is not carried out automatically even if an impact of a predetermined strength or greater on the handheld device 12 is detected.

After that, the processing returns to step S51 and the processing of step S51 and onward is executed.

Also, if it is determined in step S55 that an impact of a predetermined strength or greater is not detected, the processing returns to step S51. After that, the processing of step S51 and onward is executed.

Thus, the configuration to carry out automatic reporting when an impact of a predetermined strength or greater is applied to the handheld device 12 inside the vehicle, and not to carry out automatic reporting when an impact of a predetermined strength or greater is applied to the handheld device 12 outside the vehicle, is provided. Therefore, when an accident has occurred to the vehicle 2, reporting to the center 3 can be carried out securely and erroneous reporting in the case where no accident has occurred can be prevented. Thus, accuracy of automatic reporting is improved.

Also, the automatic reporting mode and the normal mode are switched automatically, based on the result of inside/outside determination by the handheld device 11, without the user having to carry out any particular operation. Therefore, convenience for the user is improved. Moreover, failure by the user to set the automatic reporting mode and hence failure to execute automatic reporting at the occurrence of an accident can be prevented.

Figure 5:
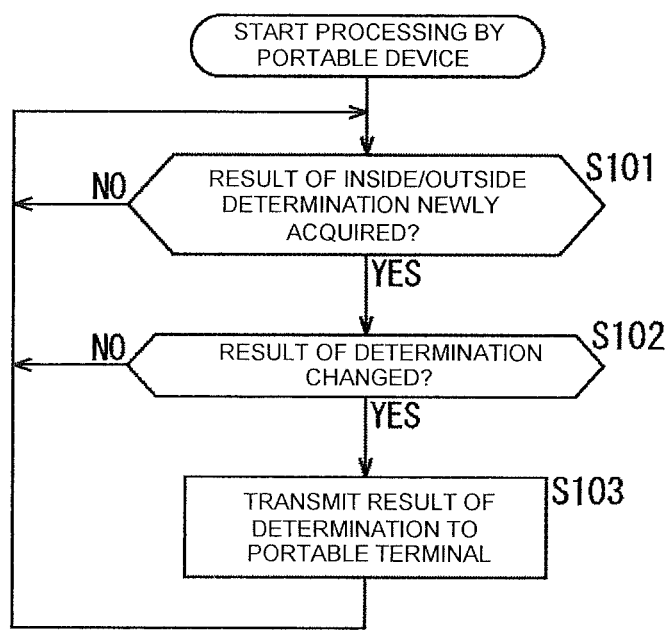
FIG. 5 is a flowchart for explaining a second embodiment of processing by a handheld device.

Next, a second embodiment of the processing by the handheld device 11 will be described with reference to the flowchart of FIG. 5.

In step S101, whether the result of inside/outside determination is newly acquired or not is determined, as in the processing of step S1 in FIG. 2. If it is determined that the result of inside/outside determination is newly acquired, the processing goes to step S102.

In step S102, the inside/outside determination unit 21 determines whether the result of the determination is changed or not. Specifically, if the result of the previous determination indicates being inside the vehicle and the result of the determination of this time indicates being outside the vehicle, the inside/outside determination unit 21 determines that the result of the determination is changed, and the processing goes to step S103.

In order to prevent erroneous determination, for example, it may be determined that the result of the determination is changed, if the same result of the determination continues a predetermined number of times after the result of the determination is changed. Also, even if the result of the determination is not changed, information of the present inside/outside determination may be transmitted periodically to the handheld device 12.

In step S103, the result of the determination is transmitted to the handheld device 12, as in the processing of step S2 of FIG. 2.

After that, the processing returns to step S101 and the processing of step S101 and onward is executed.

Meanwhile, if it is determined in step S102 that the result of the determination is not changed, the processing returns to step S101 without transmitting the result of the determination to the handheld device 12, and the processing of step S101 and onward is executed.

In this way, the number of times of communication between the handheld device 11 and the handheld device 12 can be reduced. Therefore, power consumption by the handheld device 11 and the handheld device 12 can be reduced.

2. Modifications

Hereinafter, modifications of one or more embodiments of the invention will be described.

For example, a change from the automatic reporting mode to the normal mode requires less accuracy and immediacy than a change from the normal mode to the automatic reporting mode. Therefore, for example in the processing by the handheld device 11 shown in FIG. 2, if the state where the result of the determination indicates being outside the vehicle continues, after the result of the determination is transmitted from the handheld device 11 a predetermined number of times, the transmission may be stopped or the frequency of the transmission may be lowered.

Also, for example, it is possible to carry out inside/outside determination between the vehicle 2 and the handheld device 12, using the short-range communication function of the handheld device 12. However, accuracy of the inside/outside determination is expected to rise if the handheld device 11 used exclusively in the vehicle 2 is used.

Moreover, for example, by integrating the functions of the handheld device 11 and the handheld device 12 shown in FIG. 1 into one of these, the single handheld device or handheld device may singlehandedly carry out acquisition of information of inside/outside determination and reporting to the center 3.

Figure 6:
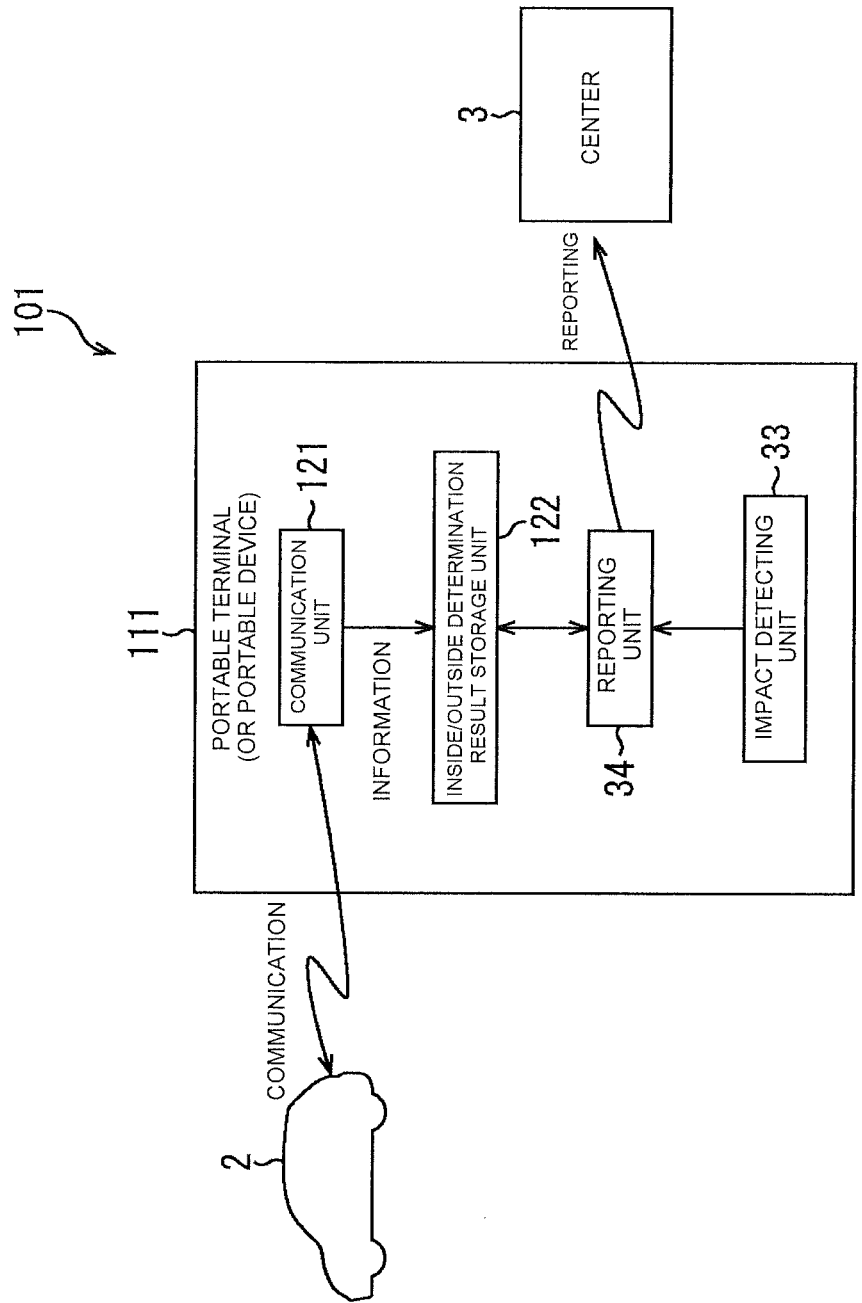
FIG. 6 is a block diagram showing a first modification of the reporting system of one or more embodiments of the present invention.

FIG. 6 shows an example of the configuration of a reporting system 101 using a handheld device 111 (or handheld device 111) in which the functions of the handheld device 11 and the handheld device 12 shown in FIG. 1 are integrated. Hereinafter, the handheld device 111 having the functions of the handheld device 11 installed on the handheld device side will be described. However, the handheld device 111 having the functions of the handheld device 12 installed on the handheld device side carries out similar processing. In FIG. 6, the parts corresponding to those shown in FIG. 1 are denoted by the same reference numerals and duplicate explanation of the same processing is omitted where appropriate.

The handheld device 111 has a communication unit 121 which carries out communication with the vehicle 2, and an inside/outside determination result storage unit 122 which stores the result of inside/outside determination on whether the terminal itself (handheld device 111) is inside the vehicle or outside the vehicle, based on the communicated information, in addition to the impact detecting unit 33 and the reporting unit 34.

The inside/outside determination may be carried out by the vehicle 2 or by the handheld device 111. In the former case, for example, the communication unit 121 receives information of the inside/outside determination from the vehicle 2, and the inside/outside determination result storage unit 122 stores the received information. Meanwhile, in the latter case, the communication unit 121 or the inside/outside determination result storage unit 122 carries out the inside/outside determination, based on the communication state with the vehicle 2 or the like, and the inside/outside determination result storage unit 122 stores information of the inside/outside determination that is acquired.

Figure 7:
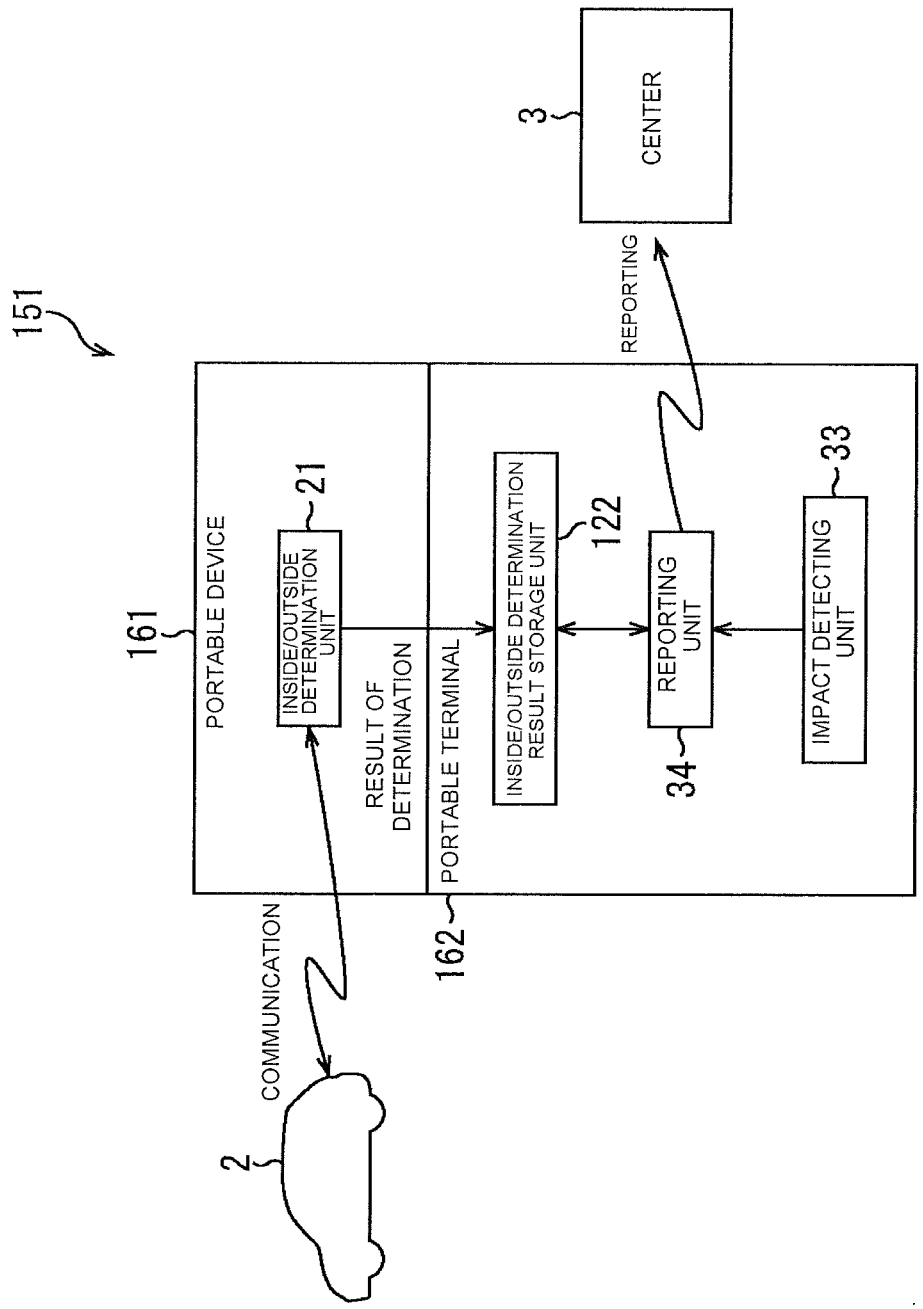
FIG. 7 is a block diagram showing a second modification of the reporting system of one or more embodiments of the present invention.

It is also possible, for example, to use wired communication for the communication between a handheld device 161 and a handheld device 162, as in a reporting system 151 of FIG. 7. In FIG. 7, the parts corresponding to those in FIGS. 1 and 6 are denoted by the same reference numerals and duplicate explanation of the same processing is omitted where appropriate.

The handheld device 161 can be connected to the handheld device 162, for example, using a predetermined cable or the like, or can be inserted into a connection terminal of the handheld device 162 (for example, a connection terminal of a charger or earphone) or the like and thus integrated with the handheld device 162. The inside/outside determination unit 21 of the handheld device 161 supplies the result of the inside/outside determination to the inside/outside determination result storage unit 122 of the handheld device 162 via wired communication and causes the inside/outside determination result storage unit 122 to store the result of the inside/outside determination.

Also, for the communication between the handheld device 12 and the center 3, for example, communication via a network such as the Internet through a wireless router or the like based on WiFi or the like can be used, other than mobile communication through a base station.

Example of Configuration of Computer

The above series of processing can be executed by hardware or by software. If the series of processing is executed by software, a program forming the software is installed in a computer. Here, the computer may include a computer incorporated in dedicated hardware, or, for example, a general-purpose personal computer or the like configured to execute various functions by installing various programs therein.

The program executed by the computer can be recorded in a removable medium and thus provided, for example, as a package medium or the like. Also, the program can be provided via a wired or wireless transmission medium such as local area network, CAN (controller area network), the Internet, or digital satellite broadcast.

In addition, the program can also be installed in advance, for example, in a ROM or storage unit.

The program executed by the computer may be a program in which processing is carried out in time series along the order explained in this description, or may be a program in which processing is carried out in parallel or at necessary timing such as when access is made.

In this description, a system refers to an aggregate of plural components (devices, modules (components) and the like) and it does not matter whether all the components are in the same casing or not. Therefore, both plural devices housed in separate casings and connected to each other via a network, and a single device having plural modules housed in a single casing, are systems.

Moreover, possible embodiments of the invention are not limited to the above embodiments and various changes can be made without departing from the scope of the invention.

Also, each step explained in the flowcharts can be executed by a single device or can be divided and executed by plural devices.

Moreover, if one step includes plural processings, the plural processings included in the one step can be executed by a single device or can be divided and executed by plural devices.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A reporting system comprising:
   a first handheld device that locks and unlocks a door of a vehicle; and
   a second handheld device that communicates with the first handheld device,
   wherein the first handheld device comprises:
   an inside/outside determination unit that carries out wireless communication with the vehicle via one or more antennas provided on the vehicle and acquires, from the vehicle, information of inside/outside determination on whether the first handheld device is inside the vehicle or outside the vehicle; and
   a transmitting unit that transmits the result of the inside/outside determination, and
   wherein the second handheld device comprises:
   a receiving unit that receives the result of the determination from the first handheld device;
   a mode setting unit that sets a first mode in which automatic reporting about a vehicle accident is carried out, if the result of the determination indicates being inside the vehicle, and that sets a second mode in which the automatic reporting is not carried out, if the result of the determination indicates being outside the vehicle;
   an impact detecting unit that carries out detection of an impact on the second handheld device; and
   a reporting unit that carries out the automatic reporting when an impact of a predetermined strength or greater on the second handheld device is detected in the case where the first mode is set.

2. The reporting system according to claim 1,
   wherein the first handheld device is a vehicle key FOB used for a remote control to lock and unlock the door of the vehicle, and
   wherein the second handheld device is a mobile phone.

3. The reporting system according to claim 2,
   wherein the first mode is a state were an application program to carry out the automatic reporting is started up, and
   wherein the second mode is a state where the application program is not started up.

4. The reporting system according to claim 1,
   wherein the communication between the first handheld device and the second handheld device is short-range wireless communication, and
   wherein the second handheld device carries out the automatic reporting to a predetermined center via a mobile communication network.

5. The reporting system according to claim 1,
   wherein the inside/outside determination unit receives the result of the determination from the vehicle.

6. The reporting system according to claim 1,
   wherein the inside/outside determination unit carries out the inside/outside determination based on the result of wireless communication with the vehicle.

7. The reporting system according to claim 2,
   wherein the communication between the first handheld device and the second handheld device is short-range wireless communication, and
   wherein the second handheld device carries out the automatic reporting to a predetermined center via a mobile communication network.

8. The reporting system according to claim 3,
   wherein the communication between the first handheld device and the second handheld device is short-range wireless communication, and
   wherein the second handheld device carries out the automatic reporting to a predetermined center via a mobile communication network.

9. The reporting system according to claim 2,
   wherein the inside/outside determination unit receives the result of he determination from the vehicle.

10. The reporting system according to claim 3,
    wherein the inside/outside determination unit receives the result of the determination from the vehicle.

11. The reporting system according to claim 4,
    wherein the inside/outside determination unit receives the result of the determination from the vehicle.

12. The reporting system according to claim 2,
    wherein the inside/outside determination unit carries out the inside/outside determination based on the result of wireless communication with the vehicle.

13. The reporting system according to claim 3,
    wherein the inside/outside determination unit carries out the inside/outside determination based on the result of wireless communication with the vehicle.

14. The reporting system according to claim 4,
    wherein the inside/outside determination unit carries out the inside/outside determination based on the result of wireless communication with the vehicle.

15. A reporting control method comprising:
    an inside/outside determination step and a transmission step executed by a key FOB used to lock and unlock a door of a vehicle; and
    a receiving step, a mode setting step, an impact detection step, and reporting step executed by a handheld device that communicates with the key FOB,
    wherein the inside/outside determination step comprises:
    carrying out wireless communication with the vehicle via one or more antennas provided on the vehicle, and
    acquiring, from the vehicle, information about inside/outside determination on whether the key FOB is inside the vehicle or outside the vehicle:
    wherein the transmission step comprises:
    transmitting a result of the inside/outside determination,
    wherein the receiving step comprises:
    receiving the result of the determination from the key FOB,
    wherein the mode setting step comprises:
    setting a first mode in which automatic reporting about a vehicle accident is carried out, if the result of the determination indicates being inside the vehicle, and
    setting a second mode in which the automatic reporting is not carried out, if the result of the determination indicates being outside the vehicle,
    wherein the impact detection step comprises:
    detecting an impact on the handheld device, and
    wherein the reporting step comprises:
    carrying out the automatic reporting when an impact of a predetermined strength or greater on the handheld device is detected in the case where the first mode is set.

16. A handheld device comprising:
a receiving unit that receives information about inside/outside determination on whether a key FOB used to lock and unlock a door of a vehicle is inside the vehicle or outside the vehicle, from the key FOB, wherein the key FOB acquires the information about the inside/outside determination based on wireless communication with the vehicle;
a mode setting unit that sets a first mode in which automatic reporting about a vehicle accident is carried out, if the key FOB is inside the vehicle, and that sets a second mode in which the automatic reporting is not carried out, if the key FOB is outside the vehicle;
an impact detecting unit that carries out detection of an impact; and
a reporting unit that carries out the automatic reporting when an impact of a predetermined strength or greater on the impact detecting unit is detected in the case where the first mode is set.

17. The handheld device according to claim 16, wherein the first mode is a state where an application program to carry out the automatic reporting is started up, and the second mode is a state where the application program is not started up.

\* \* \* \* \*